United States Patent [19]
Gibbs

[11] Patent Number: 5,762,639
[45] Date of Patent: Jun. 9, 1998

[54] DEVICE FOR TARGETED, CATHERIZED DELIVERY OF MEDICATIONS

[76] Inventor: David E. Gibbs, 13 Richmond Road, Ottawa, Ontario, Canada, K1Y 2X1

[21] Appl. No.: 471,372

[22] Filed: Jun. 6, 1995

[51] Int. Cl.⁶ .................................................. A61M 5/32
[52] U.S. Cl. .................. 604/272; 604/264; 606/80; 606/180
[58] Field of Search ..................... 604/264, 267, 604/272, 274; 606/80, 180, 159–170; 433/89, 90, 165, 197, 198

[56] References Cited

U.S. PATENT DOCUMENTS

| | | | |
|---|---|---|---|
| 1,123,730 | 1/1915 | Greenfield | 433/165 |
| 2,317,648 | 4/1943 | Sigveland | 433/80 |
| 4,306,570 | 12/1981 | Matthews | 128/754 |
| 4,678,471 | 7/1987 | Noble et al. | 623/16 |
| 4,747,824 | 5/1988 | Spinello | 433/89 |
| 4,944,677 | 7/1990 | Alexandre | 433/165 |
| 5,057,013 | 10/1991 | Dillon | 433/165 |
| 5,261,877 | 11/1993 | Fine et al. | 604/49 |
| 5,312,345 | 5/1994 | Cole | 604/267 |
| 5,312,375 | 5/1994 | Gurmarnik | 604/264 |
| 5,341,816 | 8/1994 | Allen | 606/179 |
| 5,406,940 | 4/1995 | Melzer et al. | 128/6 |
| 5,423,823 | 6/1995 | Schneiding | 606/80 |
| 5,423,824 | 6/1995 | Akerfeldt et al. | 606/80 |

*Primary Examiner*—Michael Powell Buiz
*Assistant Examiner*—Bhisma Mehta
*Attorney, Agent, or Firm*—Thomas R. Vigil

[57] ABSTRACT

Apparatus and method for catheterized delivery or infusion of medication and anaesthesia are disclosed. The perforating catheter is first used to perforate the periodontal ligament and/or the cortical plate of bone tissue, and is then left in place and used as a catheter for insertion of a hypodermic needle of smaller gauge to deliver medication or anaesthesia to a target area. The perforator is a bevelled needle for drilling into the ligament or bone tissue. For drilling, the device comprises an adaptor which transmits the rotational movement from a dental hand piece or the like to the bevelled needle. A cap is also included for protecting the bevelled needle during storage of the device. The adaptor may have a rod which extends axially into the bevelled needle when the device is assembled for drilling. The rod is used to prevent the debris resulting from drilling from blocking the passage in the bevelled needle. As well, the rod reinforces the needle and maintains the alignment between the perforator and the adaptor for improved drilling efficiency.

11 Claims, 3 Drawing Sheets

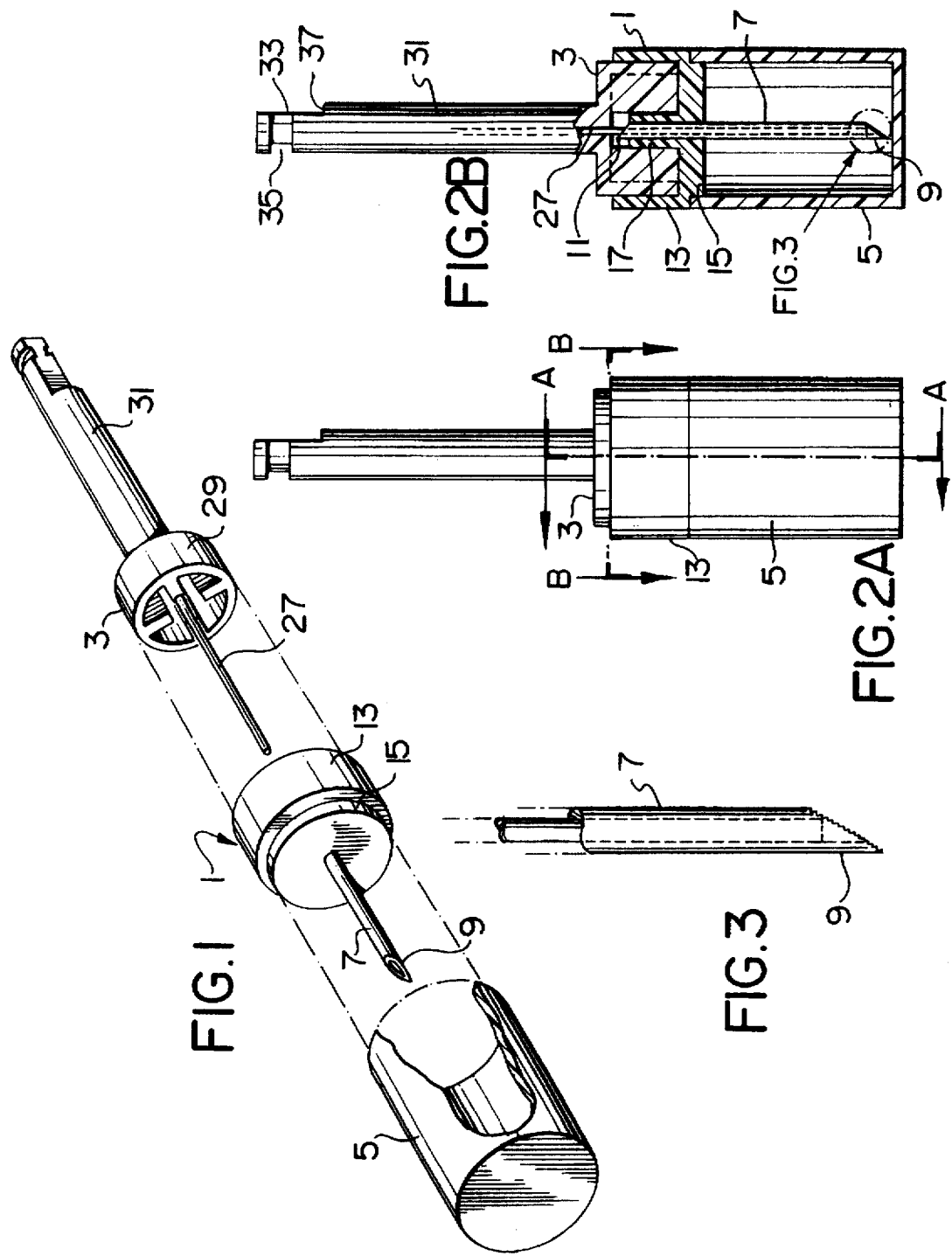

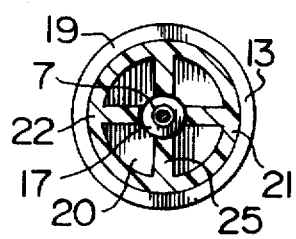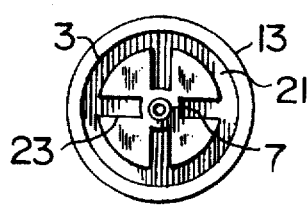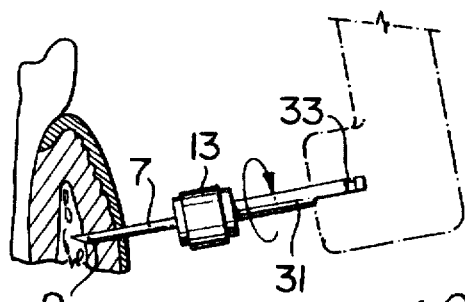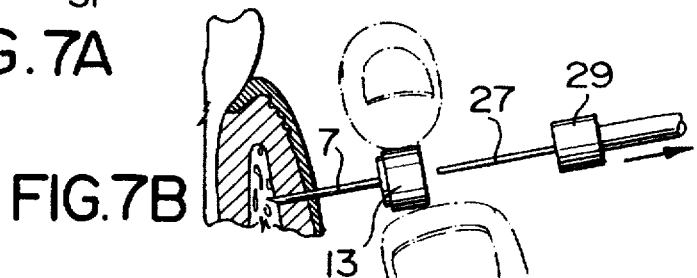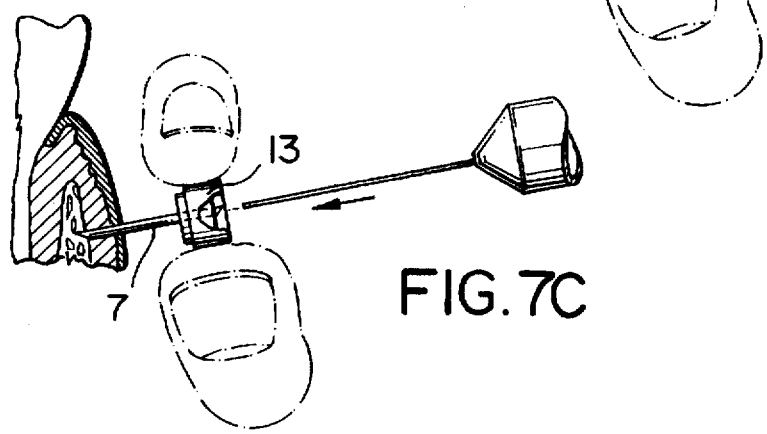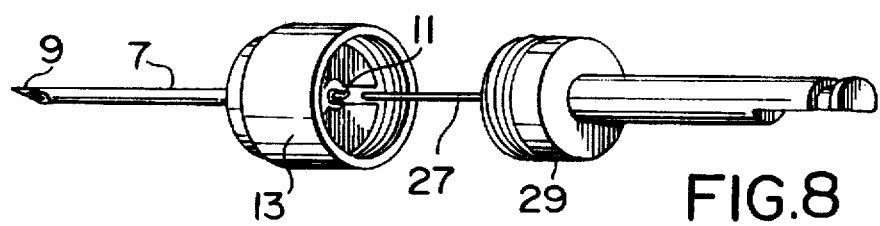

ically significantly, for the threaded sleeve to be securely fastened

DEVICE FOR TARGETED, CATHERIZED DELIVERY OF MEDICATIONS

BACKGROUND OF THE INVENTION

1. Field of the Invention

The present invention provides for a simple method and device for infusing or injecting medication; it is applicable to medical or dental and the like procedures. More particularly, the invention is directed to catheterized delivery of anaesthesia and other medication. More particularly still, it is directed to catheterized delivery of dental anaesthetic to a targeted nerve and to an apparatus for such delivery.

2. Related Art

There are a variety of methods currently in use for providing local anaesthetic in dentistry. These methods and apparatuses however all have disadvantages, either being difficult for practitioners to perform or painful and unpleasant to the patient.

An example of a method used currently in dentistry is the infiltration method, whereby a local anaesthetic solution is injected into the soft tissue of gingiva. In doing so, the solution eventually passes through the cortical plate affecting the nerve bundle entering the tooth. Disadvantages of this method include the delay of onset of anaesthesia after the injection and, in most cases, ballooning of the injected tissue. As well, there is an extended period of time for recovery of the tissue until return to normal condition.

Another method which is currently used is the regional block method whereby an anaesthetic solution is injected locally in proximity to the nerve trunk as it enters the bone. Disadvantages of this procedure are that it is extremely difficult to locate the nerve trunk, there is discomfort to the patient and a delay for the anaesthetic to take effect. As in the case of the infiltration method, this method necessitates a long recovery period for tissue to return to normal.

At present, two types of apparatus have been used to perform intra-osseous anaesthesia. These are surgical burs used to perforate the cortical plate and the villet injectors.

The use of a surgical bur has disadvantages in that burs are expensive and they have to be sterilized between uses or a new bur used each time. In addition, the method is slow, requiring the attached gingiva and periosteum to be anaesthetized before the cortical plate is perforated. The villet injector is an apparatus that serves both as a perforator and injector. It uses specially designed needles rotated by a conventional dental motor. A disadvantage of this device is that the needle often becomes clogged with pulverized bone which obstructs the passage in the needle and prevents injection of the anaesthetic solution. It is generally difficult to remove the clogging material from the needle and often the use of a second needle is necessary. Other disadvantages of this method include the initial capital cost of the instrument purchase, and the cost of the needles which are somewhat expensive. In addition, the design of the instrument makes access to various parts of the mouth difficult and sometimes impossible.

Intra-osseous and targeted root-canal nerve anaesthesia have not become popular for the reason that there has not been a practical technique of making the injections successfully. For example, there has been a general belief that this method is radical and to be restored to only if nerve block and infiltration anaesthetic do not accomplish the desired result. However, intra-osseous and targeted injections produce positive, more profound anaesthesia and could be made with less pain than either of the other types according to the present invention.

Targeted anaesthesia has several advantages over prior art nerve block or infiltration methods. There is no feeling of numbness in the tongue, cheek, or lips during or after the injection and there is no after-pain. The anaesthetic is profound and acts immediately alleviating the necessity of waiting for the anaesthetic to take effect as with the nerve block and infiltration methods. Furthermore, as only a few drops of anaesthetic are injected, there is no feeling of faintness or increasing of the pulse rate.

To achieve targeted anaesthesia one must gain access, if intra-osseous, to the cancellous bone by going through the cortical layer; or to the bottom of the tooth, if root-canal targeted anaesthesia is desired. Because of instant anaesthesia and profound pulpal anaesthesia, there is a much greater control over the region one wishes to anaesthetize, resulting in a much smaller dose of anaesthetic; as well as, of course, other medication, where applicable.

U.S. Pat. No. 5,173,050 (Dillon) discloses a dental apparatus for perforating the cortical plate of human maxillary and mandibular bones. The apparatus of Dillon comprises a metal needle moulded into a plastic shank. The shank is being formed with means for cooperation with a dental hand piece for transmitting the rotational movement to the needle. The needle used for drilling is solid and has a sharp bevelled free end. The apparatus described by Dillon is disposable.

However, the device disclosed in Dillon's patent cannot be used as a catheter for injecting anaesthetic by inserting a hypodermic needle through the drilling needle. As well, the device disclosed by Dillon is not provided with means for blocking entry of bone debris into the needle passageway. In addition, the direct connection between the hand piece and the perforator does not provide for a safe and reliable barrier against bacteria passing from the needle to the hand piece.

U.S. Pat. No. 3,534,476 (Winters) discloses a drilling and filling root canal apparatus. The drilling is performed by a drill having a central bore. The depth of the root canal is determined in advance and a stop is placed on the drill to limit the depth of drilling. The device is provided with a flexible rod which is pushed into the root canal so that the drill is directed along this road to follow the contour of the canal so that resulting bore will have an uniform diameter which is free of shoulders or ledges. The apparatus disclosed by Winters is concerned with enlarging the root canal after the nerve has been extracted. This apparatus is not used for injecting medication in close proximity to a targeted area for treatment or anaesthetic.

U.S. Pat. No. 4,944,677 (Alexandre) discloses a smooth hollow needle with a bevelled point for drilling a hole into the jawbone near the apex of the tooth to be anaesthetized. Thereafter, the drilling device 13 removed from the jaw, and a hypodermic needle of substantially the same gauge is inserted into the hole and anaesthesia is injected. Thus, there is no cathetized delivery of medication, with the attendant disadvantage that the pre-drilled hole may be difficult to locate when inserting the hypodermic needle.

One significantly older United States patent that is discussed by Alexandre (above) is U.S. Pat. No. 2,317,648 (Siqveland) granted in 1943. In addition to the disadvantage mentioned by Alexandre, the fact that Siqveland teaches use of threaded sleeve which penetrates the bone during drilling and is left (screwed) in the bone to serve as a guide for insertion of the actual injection needle. Due to the cost of such a device, it cannot be made disposable; but more importantly, for the threaded sleeve to be securely fastened in the bone it would have to rotate at a much slower speed than the drill (as in Siqveland) or the drilling catheter (as in the present invention).

SUMMARY OF THE INVENTION

The present invention endeavours to mitigate the problems and disadvantages of delivering dental anaesthetic encountered with the prior art methods and devices.

The present invention provides a perforator having a central passage, which perforator then remains in place as a catheter for allowing a hypodermic needle to be inserted through the passage to deliver the desired medication. The preferred apparatus is provided with means for obstructing the entry of debris in the perforator's passage.

According to an apparatus aspect of the present invention, a device for cathetized delivery of medication comprises: a hollow drilling catheter means for penetrating ligament, tissue or bone and adapted to remain in place after drilling; and means for engaging and disengaging the drilling catheter to and from a rotary drive shaft.

In a further aspect, the rotary drive shaft comprises an axial rod adapted to be inserted into the hollow drilling catheter when engaging it.

According to another aspect of the present invention, there is provided a device for perforating the periodontal ligaments, cortical plate of small bones, and the like, for injecting substances at a predetermined site, comprising: a perforator for drilling a hole into the ligament, bone or tissue, wherein said perforator is provided with an inner passage to form a catheter adapted to remain in the hole perforated for directing a hypodermic needle to said predetermined site, and an adaptor for latching in a latching-type powered dental handpiece for transmitting rotational movement to said perforator.

The catheterized intra-osseous delivery system of the present invention comprises a perforator with a bevelled drilling needle that is used as a drill and a catheter. The needle is attached at one end to a plastic or metal body. For drilling, the body is attached to a matching adaptor provided with a driving shank which is rotated by a conventional contra angle or straight dental hand piece. Then, the perforator is used as a catheter, whereby a hypodermic needle is inserted through the drilling needle without losing access to the already perforated bone.

In the preferred form of the invention the apparatus is disposable. Before disposal, the perforator receives a cap over the needle for protection against accidental contamination of environment.

The present invention also provides a method of medical treatment, comprising the steps of: inserting a catheter, at a point in the gingival sulcus between outer tooth surface and marginal gingiva, or through gingiva and cortical plate, to a predetermined depth; and injecting medication or anaesthesia through said catheter.

Advantageously, the system of the present invention provide users with a more secure and less painful method and device for direct access for injecting medication to a target area into the cortical plate of the bone.

In addition, the system facilitates and adds a level of security previously unavailable for the anaesthetic in that it has a sure and immediate effect.

Another advantage of this system is that it provides benefits to the dentists by facilitating the use of a low cost, disposable device.

Still another advantage of this invention is that the risk of contamination is lower than with the current devices. This is because the device is disposable and because the risk of the dental equipment used with the device of the invention becoming contaminated is low.

BRIEF DESCRIPTION OF THE DRAWINGS

These and other features of the invention will become more apparent from the following description of the preferred embodiments, in which reference is made to the appended drawings, wherein:

FIG. 1 illustrates an exploded view of the device showing the component parts and their inter-relationship;

FIG. 2A illustrates the device assembled for drilling;

FIG. 2B Illustrated a longitudinal cross-section through the device illustrated in FIG. 2A, taken along line A—A of FIG. 2A;

FIG. 3 shows a detailed view of the area marked on FIG. 2B;

FIG. 4 is a cross-sectional view of the body of the perforator taken along lines B—B of FIG. 2;

FIG. 5 is a cross-sectional view of the adaptor body;

FIG. 6 is a cross-sectional view of the cap;

FIGS. 7A–7C illustrate the method according to the invention. FIG. 7A shows the device drilling, in the bone tissue; FIG. 7B shows the perforator inserted into the bone tissue and the adaptor de-coupled; and FIG. 7C shows the perforator inserted into the bone tissue as a catheter and a hypodermic needle set for delivering an injection;

FIG. 8 illustrates another embodiment of the invention;

DETAILED DESCRIPTION OF THE PREFERRED EMBODIMENT

Figures 9, 10:
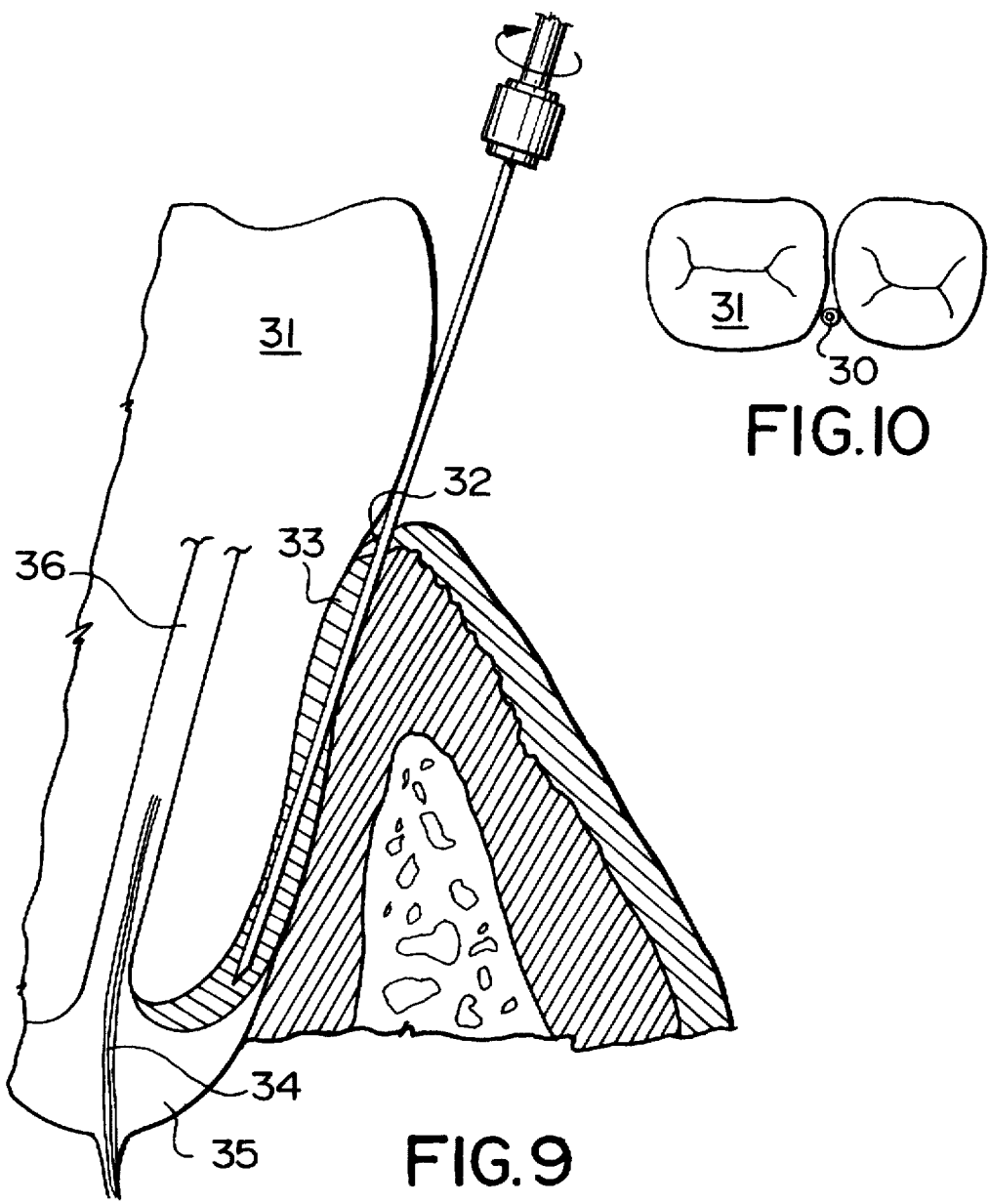
FIG. 9 illustrates an alternative method of delivery medication to treat a root-canal nerve.
FIG. 10 illustrates from a plan view the point of catheter insertion for the alternative method shown in FIG. 9.

FIG. 1 illustrates an exploded view of the device showing the component parts and their inter-relationship. The device comprises a perforator 1, an adaptor 3 and a cap 5.

The perforator 1 has a bevelled drilling needle 7 which is used both as a drill and a catheter. Needle 7 is bevelled at both ends, as better shown on FIG. 2B. The first end 9 is formed as a drilling tip in that it has cutting teeth along the edge, as shown in FIG. 3. The second end 11 is bevelled for receiving and directing the needle of a hypodermic syringe and for easy coupling with the adaptor 3, as will be seen later.

A flange 13 is fixed on the needle about the second end 11, so that the needle passes along the geometrical axis of the flange 13. The flange 13 is manufactured or moulded of a plastic or other material, and it has a generally cylindrical outer shape. This shape is preferred as the flange 13 rotates together with the needle 7 for drilling. Variations of the shape illustrated in the attached drawings may also be contemplated.

The flange 13 is adapted for receiving cap 5 at one end and for coupling with the adaptor 3 at the other end. As an example, a collar 15 may be provided on the flange 13 so that the cap 5 holds over the collar 15 when pressed. The cap 5 is needed to protect and cover the tip 9 of the needle 7 before use and when the device is disposed of.

For ease of manipulation the internal diameter of the cap 5 and the external diameter of the collar 15 should be as large as is reasonable and preferably between 10 to 20 times greater than the diameter of the needle 7. Another advantage of the collar 15 is that it provides a stop to limit the depths of penetration of the needle 7 (the depth of penetration of the needle 7 is, therefore, termed the drilling length, as opposed to the remaining length of the needle 7, which is termed the attachment length). The flange 13 is shaped to form an inner axial shaft 17 projecting from the centre of the collar 15, and a female connector 19 for coupling with a corresponding male connector provided in the adaptor 3.

The coupling between the perforator and the adaptor is illustrated on FIGS. 2B, 4 and 5. FIG. 2B shows a longitudinal section of a female connector 19 provided in the flange 13 and a male connector 21 provided in the adaptor 3. FIG. 4 illustrates a cross-section of an exemplary female connector 19, while FIG. 5 shows a cross-section of the corresponding male connector 21. The male connector is provided with radial ribs 23, extending towards the centre but not meeting to leave room for the central shaft 17, while corresponding grooves 25 are provided in the female connector, alternating with islands 20. The female connector is also formed with a clearance ring 22 for accommodating the thickness of the body 29 of the adaptor.

The tubular shaft 17 forms a reinforced passage for drilling needle 7. The shaft also provides enough contact surface between the drilling needle and the body to ensure that these two parts rotate together during drilling. As could be seen on FIG. 2B, end 11 of the needle is bevelled and extends a little over the shaft 17, but there is a clearance between the tip of end 11 and the male connector when the device is assembled for drilling.

When rotated, the drilling needle 7 penetrates in the bone tissue through gingiva or ligament and drills a hole with the cutting tip 9. The perforator 1 may remain in place as a catheter, with the drilling needle inserted into the bone. Then, a hypodermic needle may be introduced through the passage of drilling needle 7 to inject a medicament directly into the bone. Therefore, the drilling needle 7 is selected to have a wide enough passage for allowing a hypodermic needle with a smaller gauge to be inserted through needle 7.

The adaptor 3 has three functions. Firstly, the adaptor conveys the rotational movement from a dental hand piece or the like to the perforator. As well, the adaptor is provided with means for blocking bone debris for entering into the syringe passage and also aligns and reinforces the needle 7 during drilling.

The adaptor includes a rod 27, a body 29 and a shank 31.

Body 29 includes male connector 21 which is formed, as indicated above, with longitudinal ribs 23 which couple with grooves 25 of the female connector 19 for driving needle 7. The shank 31 extends along the axis of the adaptor and is formed with a joint 33 for attachment with a contra-angle or straight hand piece. The shank 31 has a groove 35 and a cut-out 37 to fix the shank in place in the known manner. Generally, the shank transmits to the needle 7 the rotational movement from the hand piece.

The shank 31 also acts as a barrier for contamination, at it is generally thought that bacteria is reluctant to change direction, and there are a plurality of 90° angles between the tip 9 of drilling needle 7 and the joint 33.

The rod 27 has the diameter and length selected in accordance with the size of needle 7. The rod 27 is fixed in the geometrical centre of body 29 so as to readily penetrate into the hollow passage of the needle, when the device is assembled for drilling. When the rod 27 is inserted within the needle passage, it advances through the length of the needle up to the bevelled end, as shown on FIGS. 2A and 3 in dotted lines. In this way, the debris from drilling cannot penetrate to block the needle passage. In addition, the rod gives additional rigidity, strength and alignment to needle 7 during drilling. The rod also advances through the a portion of the shank as is illustrated in FIG. 2B in dotted lines.

FIG. 8 illustrates an alternative embodiment of the present invention. In this variant, body 13 is provided with an internal thread while body 29 is provided with a matching external thread. By threading one to the other and using the central rod 27 to align the two bodies together, the perforator could be driven by the hand piece in a similar manner as in the variant disclosed above. Of course, the thread is going in an opposite direction to the direction of rotation of the device for avoiding disconnection of the two bodies.

An alternative method of targeted delivery is shown in FIGS. 9 and 10. The perforator 7 is inserted at a point 30 between teeth, parallel to the tooth 31 in treatment, and penetrates through gingival sulcus 32 and ligament 33 to a depth near the entry of the nerve, artery and vein bundle 34 through the bone 35 and into the tooth-root canal 36. This method of targeted delivery, say, of anaesthesia is suitable, where perforating vertical to the tooth through gingiva and cortical bone is not convenient or possible; as in the case of rear molars.

There are a variety of ways that this invention can be devised but the end result is to perform catheterized intra-osseous delivery system.

The device of this invention operates as follows:

First, a site for the injection is selected by the practitioner. The gingiva over the injection side is disinfected and topically anaesthetized. A small amount of anaesthetic solution is injected until blanching of the tissue, and this will anaesthetize the gingiva and the periosteum. The following operations are illustrated in FIGS. 7A, 7B and 7C, and FIGS. 9 and 10.

As can be seen in FIG. 7A, the bevelled end 9 of the needle 7 is placed against the gingiva and shank 31 is attached with joint 33 to a contra angle or to a straight dental hand piece. The adaptor and perforator are coupled for drilling. The perforator should be held perpendicular to the cortical plate, or if not possible or convenient, it should be held vertical and parallel to the long axis of the tooth as shown in FIG. 9, having been inserted between teeth as shown in FIG. 10. The perforator is then operated in small bursts of rotation from the hand piece until resistance is no longer felt, as is well known to dentists.

Next, the adaptor 3 is removed from the engagement with perforator 1 by applying pressure to the body 13 with the fingers thus keeping the needle 7 in the perforated cortical plate. This is shown in FIG. 7B.

The presence of the needle 7 in the cortical plate, or down the side of the tooth as in FIG. 9, allows an injection to be made without complicated manoeuvres to find the perforation in the case of floating gingiva or the free or marginal gingiva. FIG. 7C illustrates the next step, namely how the injection needle is inserted through the perforator 1 for delivering the anaesthetic solution required.

The last step is to remove the perforator 1 from the cortical plate and reinstall the cover cap 5 over the needle 7, then insert the adaptor to the perforator making the unit complete and disposable. The cap 5 provides a means whereby the apparatus may be removed from the dental hand piece without any risk of the user being in contact with body fluids which will be present on the needle after use. This is extremely important particularly since there may be a risk of contacting Aids or Hepatitis should the user accidentally prick a finger with the needle. It is therefore desirable that the cap should be of a hard or rigid rubber or plastic material not easily penetrated by the needle.

What is claimed is:

1. A device for perforating the periodontal ligaments, cortical plate or small bones, and the like and for injecting substances at a predetermined site, comprising:

perforator for drilling a hole into the ligament, bone or tissue, wherein said perforator is provided with an inner passage to form a catheter adapted to remain in the hole perforated for directing a hypodermic needle to the predetermined site, and an adaptor at one end of the perforator for latching a latching-type powered dental handpiece thereto for transmitting rotational movement to said perforator;

a first connector formed inside a first body of a generally cylindrical outer shape, for cooperation with said adaptor;

a drilling needle extending from said first body along its axis of rotation opposite said first connector, said drilling needle being fixed to said first body;

said adaptor comprising a second connector formed inside a second body of a generally cylindrical outer shape; a driving shank extending along a rotational axis of said second body, said shank having two ends, one end fixed to said second body opposite to said second connector, and the other free end adapted to receive a rotational movement; and a rod extending along the rotational axis of said second body in an opposite direction to said driving shank, said rod sized to fit into a passage in said drilling needle.

2. A device as claimed in claim 1, wherein said drilling needle has a drilling length and an attachment length, and a passage sized to accommodate a hypodermic needle of a smaller gauge.

3. A device as claimed in claim 2, wherein said drilling length ends with a cutting edge.

4. A device as claimed in claim 3, wherein said cutting edge is bevelled.

5. A device as claimed in claim 3, wherein said cutting edge is provided with cutting teeth therealong.

6. A device as claimed in claim 2, wherein said attachment length ends with a catheter end.

7. A device as claimed in claim 6, wherein said catheter end is bevelled.

8. A device as claimed in claim 1, wherein said first and said second connectors are provided with complementary configurations for engagement to each other when moved along the rotational axis towards each other.

9. A device as claimed in claim 8, wherein said first body is provided with means for receiving and securing a protective cap over said needle.

10. A device as claimed in claim 9, wherein said means for receiving and securing comprises a disc entered about said needle and fixed on said first body for receiving said protective cap.

11. A device as claimed in claim 1, wherein said rod comprises:

a anchoring part incorporated and fixed into said shank, for driving said rod to rotate with said shank; and a free part of a length selected to extend up to the beginning of the bevelled tip of said needle when the rod is inserted into said needle, for blocking entrance of debris resulting during bone perforation.

* * * * *